US011980772B2

(12) United States Patent
Hestdal et al.

(10) Patent No.: US 11,980,772 B2
(45) Date of Patent: *May 14, 2024

(54) METHOD OF PHOTODYNAMIC THERAPY (PDT) FOR BLADDER CANCER

(71) Applicant: PHOTOCURE ASA, Oslo (NO)

(72) Inventors: Kjetil Hestdal, Oslo (NO); Aslak Godal, Oslo (NO)

(73) Assignee: PHOTOCURE ASA, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 17/588,978

(22) Filed: Jan. 31, 2022

(65) Prior Publication Data

US 2022/0152411 A1    May 19, 2022

Related U.S. Application Data

(63) Continuation of application No. 16/063,142, filed as application No. PCT/EP2016/081809 on Dec. 19, 2016, now Pat. No. 11,235,168.

(30) Foreign Application Priority Data

Dec. 17, 2015   (EP) .................................... 15200938

(51) Int. Cl.
*A61N 5/06*      (2006.01)
*A61B 1/307*     (2006.01)
*A61K 41/00*     (2020.01)

(52) U.S. Cl.
CPC .......... *A61N 5/062* (2013.01); *A61K 41/0061* (2013.01); *A61B 1/307* (2013.01); *A61N 2005/061* (2013.01); *A61N 2005/0663* (2013.01)

(58) Field of Classification Search
CPC ................ A61B 1/307; A61K 41/0061; A61N 2005/061; A61N 2005/0662; A61N 2005/0663; A61N 5/062; A61P 13/10; A61P 35/00

See application file for complete search history.

(56) References Cited

U.S. PATENT DOCUMENTS

| 11,235,168 B2* | 2/2022 | Hestdal ............. A61K 41/0061 |
| 2005/0031541 A1 | 2/2005 | Gierskcky et al. |

FOREIGN PATENT DOCUMENTS

| CN | 101891639 | 11/2010 |
| CN | 101896203 A | 11/2010 |
| CN | 102802612 A | 11/2012 |
| CN | 104244804 B | 4/2017 |
| CN | 104661994 B | 8/2017 |
| JP | 2014094963 A | 5/2014 |
| WO | 96/28412 A1 | 9/1996 |
| WO | 2005/092838 A1 | 10/2005 |
| WO | 2008084241 A2 | 7/2008 |
| WO | 2009074811 A2 | 6/2009 |
| WO | 2010/142457 A1 | 12/2010 |
| WO | 2010142456 A1 | 12/2010 |
| WO | 2013092740 A1 | 6/2013 |
| WO | 2014/020164 A1 | 2/2014 |
| WO | 201479972 A1 | 5/2014 |

OTHER PUBLICATIONS

Photocure Asa, Cysview®, Highlights of Prescribing Information, Patient Couselling Information (2011); 2 pgs.
Thomas, et al., "Photodynamic Assisted Detection and Treatment of Superficial Bladder Cancer Using the Photosensitizer Cervix" Urology (2006); vol. 68 (Supplemental 5A); p. 206, Abstract.
Rink, M. et al., "Hexyl Aminolevulinate-Guided Flourescence Cystoscopy in the Diagnosis and Follow-up Patients with Non-Muscle-invasice Bladder Cancer: A Critical Review of the Current Literature", European Urology (2013) vol. 64, pp. 624-638.
Burger, M. et al., "Photodynmaic Diagnosis of Non-muscle-invasive Bladder Cancer with Hexaminolevulinate Cystoscopy: A Meter analysis of Detection and Recurrence Based on Raw Data"; European Urology (2013); vol. 64; pp. 846-854.
Witjes, J. A. et al., Clinical and Cost Effectiveness of Hexaminolevulinate-guided Blue-light Cystoscoy: Evidence Review and Updated Expert Recommendations, European Urology (2014); vol. 66; pp. 863-871.
Gakis, G. et al., "Photodynamic Diagnosis-guided TUR-BT is an Independent Predictor for Improved Recurrence-free Survival after Radical Cystectomy for Invasive Bladder Cancer"; Urology (2013); vol. 82: (3 Supplemental 1), pg. Abstract No. UP;046' p. S208.
Berger, A. P., et al., "Photodynamic Therapy with Intravesical Instillation of 5-Aminoleuvlinic Acid for Patients with Recurrent Superficial Bladder Cancer: A Single-Center Study"; Urology (2003); vol. 61; pp. 338-341.
Waidelich, R. et al., "Whole Bladder Photodynmaic Therapy with 5-Aminolevulinic Acid using a White Light Source"; Urology (2003); vol. 61, pp. 332-337.
Skyrme, R. J. "A Phase-1 Study of Sequential Mitomycin C and 5-Aminolaevulinic Acid-Mediated Photodynamic Therapy in Recurrent Superficial Bladder Carcinoma", BJU International (2005); vol. 95:5; pp. 1206-1210.
Bader, M. J., et al., "Photodynamic Therapy of Bladder Cancer—A Phase I Study Using Hexaminolevulinate (HAL)"; Urologic Oncology (2013); vol. 31, pp. 1178-1183.
Fradet, Y., et al., "A Comprasion of Hexaminolevulinate Fluorescence Cystoscopy and White Light Cystoscopy for the Detection of Carcinoma in Stiu in Patients with Bladder Cancer: A Phase III Study, Multicenter Study"; J. of Urology (2007); vol. 178; pp. 68-73.

(Continued)

*Primary Examiner* — Jon Eric C Morales
(74) *Attorney, Agent, or Firm* — Fox Rothschild LLP

(57) ABSTRACT

This invention relates to a method of photodynamic therapy (PDT) for bladder cancer and its use as an adjuvant or neoadjuvant therapy in the treatment of bladder cancer. The invention provides a composition comprising hexyl 5-ALA ester (HAL) or a pharmaceutically acceptable salt thereof for use in a method of photodynamic therapy for bladder cancer, wherein said composition is instilled into the bladder of a patient in need of such treatment and the inside of said bladder is exposed to blue light having a fluence rate of 1.5 to 12.5 mW/cm2.

26 Claims, No Drawings

(56) References Cited

OTHER PUBLICATIONS

Francois, A. et al., "How to Avoid Local Side Effects of Bladder Photodynamic Therapy: Impact of the Fluence Rate"; Journal of Urology (2013); vol. 190; pp. 731-736.

Stenzl, A. et al., "Hexaminolevulinate Guided Fluorescence Cystoscopy Reduces Recurrence in Patients with Nonmuscle Invasive Bladder Cancer"; Journal of Urology (2010); vol. 184; pp. 1907-1914.

Helander, L. et al., "Red Versus Blue Light Illumination in Hexyl 5-Anminolevulinate Photodynamic Theraphy: The Influence of Light Color and Irradiance on the Treatement Outcome in vitro"; Journal of Biomedical Optics (2014); vol. 19:8; 10 pgs.

Odrun, A. G. et al., "Effects of Hexyl 5-Aminolevulinate and Light in Rat Bladder Cancer Cells"; Abstract No. 0-29; Ther. (2008); vol. 5:1; p. 72.

\* cited by examiner

METHOD OF PHOTODYNAMIC THERAPY (PDT) FOR BLADDER CANCER

This invention relates to a method of photodynamic therapy (PDT) for bladder cancer and its use as an adjuvant or neoadjuvant therapy in the treatment of bladder cancer.

Bladder cancer is the ninth most common cancer diagnosis worldwide, with more than 330 000 new cases each year and more than 130 000 deaths per year. At any point in time, 2.7 million people have a history of urinary bladder cancer. The diagnosis of bladder cancer ultimately depends on cystoscopic examination of the bladder (cystoscopy) and histological evaluation of the resected tissue. In general, cystoscopy is initially performed in the office, using flexible instruments. At the initial diagnosis of bladder cancer, 70% of cases are diagnosed as non-muscle-invasive bladder cancer (NMIBC) and approximately 30% as muscle-invasive bladder cancer (MIBC).

If a bladder tumor has been detected during cystoscopy, the patient will undergo transurethral resection (TUR), i.e. a procedure where the bladder is visualized through the urethra and tumors and lesions are resected. In case of NMIBC, such a resection is to completely remove the tumor. In case of MIBC, such a resection is of a palliative nature. Apart from the resection of the tumor, the TUR is also carried out to enable a correct histological diagnosis of the bladder cancer by a pathologist based on examination of the resected tumor/tumor biopsies.

As a standard procedure, cystoscopy and TUR are performed using white light. However, since the use of white light can lead to missing lesions that are present but not visible, photodynamic diagnosis (PDD) is often used in such procedures. In general, PDD involves the administration of a photosensitizer or a precursor thereof (i.e. a "photosensitizing agent") to an area of interest. The photosensitizer or precursor thereof is taken up into the cells, where a precursor of a photosensitizer is converted into an active photosensitizer. Upon exposure of the area of interest to light of a suitable wavelength, the photosensitizer is excited and, upon relaxation to its ground state, fluorescence occurs, which is detected.

Hexyl 5-ALA ester (hexaminolevulinate, HAL) and its salts are such photosensitizing agents. HAL preferably penetrates rapidly proliferating cells, e.g. tumor cells, where it is converted into porphyrins, such as protoporphyrin IX (PpIX), which are photosensitizers and fluorescent compounds. Under subsequent blue-light illumination, the porphyrins emit red light and thus enable specific and accurate visualization of the tumor. Hexvix®, in the US and Canada Cysview®, (Photocure ASA/Photocure Inc/Ipsen SA) is a commercially available approved diagnostic agent that comprises HAL. As an adjunct to white light, Hexvix® is used together with blue light in the photodynamic detection of bladder cancer during cystoscopy and TUR procedures, see e.g. Cysview®, Highlights of Prescribing Information, 2011). Such photodynamic detection has become an important part of the overall management of bladder cancer, i.e. diagnosis and treatment of this condition (see e.g. Thomas et al., Urology 68, Supplement, 2006, 206).

In patients with NMIBC, HAL-guided cystoscopy and TUR has increased detection of both papillary tumors and flat carcinoma-in-situ (CIS) lesions, the latter of which are difficult to detect with white light alone. HAL-guided TUR of bladder cancer in patients with NMIBC has further reduced the rate of residual tumor after such procedures and has led to superior recurrence free survival (RFS) rates and prolonged RFS intervals compared to white light TUR alone (see Rink et al., Eur Urol 4(64), 2013, 624). It is believed that superior RFS rates in patients who underwent HAL-guided TUR of bladder cancer is due to improved detection rates and resection of otherwise undetected tumors (Burger et al., Eur Urol 5(64), 2013, 846-854). Existing European guidelines on NMIBC and several expert groups' consensus statements recommend the use of HAL-guided TUR in various settings of management of NMIBC and some even recommend its use in all NMIBC patients at initial TUR (Witjes et al., Eur Urol 1(66), 2014, 863).

Detection of all tumor lesions during TUR and the rate of residual tumor in the bladder in patients with MIBC is not an issue, the bladder is removed in its entirety anyway. Hence, TUR in patients with MIBC is usually performed with white light alone and there is no guideline recommendation of using HAL-guidance under such TURs. However, HAL-guided TUR seems to have an impact on recurrence free survival also in patients who undergo cystectomy: in 268 consecutive patients who underwent cystectomy for bladder cancer it was retrospectively investigated whether patients prior to the cystectomy had undergone HAL-guided TUR or whether TUR was carried out with white light alone. Kaplan-Meier analysis was used to estimate recurrence-free survival (RFS) and overall survival (OS). The 3-year RFS was 69.8% in patients with HAL-guided TUR and 58.2% in patients with white light TUR alone. The 3-year OS was 65.0% in patients with HAL-guided TUR and 56.6%. These results indicate that HAL-guided TUR is associated with improved RFS after cystectomy in patients with MIBC (Gakis et al., Urology Vol. 82, Issue 3, Supplement, 2013, Unmoderated Posters, UP.046).

PDT—as PDD—involves the administration of a photosensitizer or a precursor thereof (i.e. a "photosensitizing agent") to an area of interest. The therapeutic effect of PDT is based on a phototoxic reaction: the photosensitizer or precursor thereof is taken up into the cells, where a precursor of a photosensitizer is converted into an active photosensitizer. Upon exposure of the area of interest to light of a suitable wavelength, the photosensitizer is excited from a ground singlet state to an excited singlet state. It then undergoes intersystem crossing to a longer-lived excited triplet state. One of the few chemical species present in tissue with a ground triplet state is molecular oxygen. When the photosensitizer and an oxygen molecule are in proximity, an energy transfer can take place that allows the photosensitizer to relax to its ground singlet state, and create an excited singlet state oxygen molecule. Singlet oxygen is a very aggressive chemical species and will rapidly react with any nearby biomolecules. Ultimately, these reactions will kill cells, i.e. cancer cells.

PDT has been previously suggested for the treatment of bladder cancer and clinical studies have been carried out to investigate efficacy and safety of such treatment.

Berger et al., Urol 2003, 61(2), 338-341, have used PDT as first line treatment in bladder cancer patients. The precursor 5-aminolevulinic acid (5-ALA) was instilled as a solution into the bladder. PDT was carried out with red light (633 nm) with a laser system and a probe positioned in the center of the bladder to ensure that the entire inside of the bladder receives the same light dose. Light doses of 30 J/cm$^2$ and 50 J/cm$^2$ were provided over a period of 16 to 32 minutes (mean irradiation time 21 minutes). With the aforementioned light doses, the mean fluence rate (calculated as light dose divided by time [s]) was thus 23.8 and 39.7 mW/cm$^2$. Side effects in the form of irritating urinary symptoms occurred in all patients and in 13% of the patients, these symptoms did not resolve before 2 weeks.

Waidelich et al., Urol 2003, 61(2), 332-337 also used 5-ALA but chose irradiation with white light from a xenon bulb. The light was transmitted into the bladder via a glass fiber which was inserted into the working channel of a cystoscope. Centration of the tip of the fiber was done with the help of a balloon catheter which was specifically designed for the procedure on the basis of a transurethral irrigation catheter. The position to the tip of the fiber was monitored by ultrasound. PDT was performed under general anesthesia and a light dose of 100 J/cm$^2$ was provided over a period of 60 to 150 minutes (i.e. at a fluence rate of 11.1-27.7 mW/cm$^2$). From the 12 patients that were treated, all patients complained about urinary frequency and urgency that was medically treated. In 7 patients, the symptoms subsided within a week while in 5 patients, they persisted for 3 weeks Skyrme et al., BJU Int 2005, 95(5), 1206-1210, used PDT as an adjuvant bladder cancer treatment to intravesical chemotherapy with mitomycin. Subsequent to mitomycin treatment, 5-ALA PDT was carried out under general or spinal anesthesia with red laser light irradiation (635 nm) which was transmitted inside the bladder via a diffusor-tipped laser fiber that was inserted into the working channel of a cystoscope. However, centration turned out to be challenging, visualization by ultrasound proved to be difficult and treatment needed to be interrupted at 5 minutes intervals to ensure that there was neither decompression nor contact between the fiber tip and bladder wall. Light doses of 10, 15 and 25 J/cm$^2$ were provided for this treatment, at a fluence rate of 18 mW/cm$^2$. A light dose of 25 J/cm$^2$ was considered the upper limit of tolerability for this therapy in terms of side effects.

Also HAL has been used in PDT of bladder cancer. Bader et al., Urol. Oncol. Seminars and Original Investigations 31, 2013, 1178-1183, have used solutions of HAL (8 mM and 16 mM) and irradiation was carried out with white light from a xenon bulb, transmitted into the bladder via a glass fiber, which was inserted into the working channel of a cystoscope. Patients received 3 HAL PDTs each six weeks apart, which were performed under general anesthesia. A light dose of 100 J/cm$^2$ was provided, but a subset of patients received 25 J/cm$^2$ at the first treatment, 50 J/cm$^2$ at the second treatment and 100 J/cm$^2$ at the third treatment. Those patients also had local anesthesia instead of general anesthesia. Irradiation was carried out over a period of 52-100 minutes, i.e. the fluence rate range calculated based on light dose and irradiation time was from 4 mW/cm$^2$ (25 J/cm$^2$ for 100 min) to 32 mW/cm$^2$ (100 J/cm$^2$ for 52 min). Standard HAL TUR was carried out prior to each PDT procedure and any papillary tumor seen at this point was resected prior to the PDT. After PDT, the bladder was again inspected with blue light. 128 adverse effects were reported in 17 patients (about 88%) and 7 severe adverse effects were reported in 4 patients (23.5%), 2 of which were considered to relate to the PDT. Of the 17 patients included, 9 were tumor-free at 6 months (52.9%), 4 were tumor-free at 9 months (23.5%) and 2 were tumor-free at 21 months (11.8%).

The disadvantage of the methods described above is that specially designed equipment is needed to carry out PDT, which is not commercially available. Furthermore, the use of light fibers and placement of the tip of said light fibers in the center of the bladder is complicated and cumbersome, the location of the fiber tip needs to be verified by ultrasound or the PDT procedure needs to be interrupted to make sure that the fiber tip is still in the center and does not touch the bladder wall, which could lead to injuries. Further, side-effects are frequent and, depending on the PDT parameters used, may take a long time before they are resolved.

Hence there is a need for novel and improved methods of photodynamic therapy for bladder cancer.

In a first embodiment the invention provides a method of photodynamic therapy for bladder cancer, comprising the instillation into the bladder of a patient in need of such treatment of a composition comprising hexyl 5-ALA ester (HAL) or a pharmaceutically acceptable salt thereof and exposing the inside of said bladder to blue light having a fluence rate of 1.5 to 12.5 mW/cm$^2$. In a first preferred embodiment, the invention provides a method of photodynamic therapy for bladder cancer, comprising the instillation into the bladder of a patient in need of such treatment of a composition comprising hexyl 5-ALA ester (HAL) or a pharmaceutically acceptable salt thereof, and exposing the inside of said bladder to blue light having a fluence rate of 1.5 to 12.5 mW/cm$^2$, wherein said blue light is provided at light dose of 0.2 to 15 J/cm$^2$.

In an alternative first embodiment, the invention provides a composition comprising hexyl 5-ALA ester (HAL) or a pharmaceutically acceptable salt thereof for use in a method of photodynamic therapy for bladder cancer, wherein said composition is instilled into the bladder of a patient in need of such treatment, and the inside of said bladder is exposed to blue light having a fluence rate of 1.5 to 12.5 mW/cm$^2$. In a preferred alternative first embodiment, the invention provides a composition comprising hexyl 5-ALA ester (HAL) or a pharmaceutically acceptable salt thereof for use in a method of photodynamic therapy for bladder cancer, wherein said composition is instilled into the bladder of a patient in need of such treatment, and the inside of said bladder is exposed to blue light having a fluence rate of 1.5 to 12.5 mW/cm$^2$, wherein said blue light is provided at light dose of 0.2 to 15 J/cm$^2$.

Without wanting to be bound to this theory, the photodynamic therapy according to the invention seems to impact bladder cancer on different levels: if the method of the invention is carried out together with a TUR, due to a phototoxic reaction as described above, residual tumor cells, i.e. tumor cells which have not been removed during TUR and/or re-attached tumor cells, i.e. tumor cells which have been detached during the TUR but which remain in the bladder due to insufficient flushing, are killed. On the other hand, the photodynamic therapy according to the invention seems to stimulate the patient's immune system to fight the bladder cancer, see Example 3 in this application. The photodynamic therapy according to the invention can be carried out with commercially available equipment, see below, and is very well tolerated, with only few and transient adverse events (see Fradet et al., J. Urol. 2007, 178, 68-73).

The bladder cancer in the context of the invention is either muscular invasive bladder cancer (MIBC) or non-muscular invasive bladder cancer (NMIBC). In the context of the first embodiment above, the bladder cancer is preferably NMIBC, which appears as papillary tumors and flat lesions (carcinoma in situ, CIS).

The term "hexyl 5-ALA ester" (HAL) denotes n-hexyl aminolevulinate, i.e. n-hexyl 5-amino-4-oxo-pentanoate.

The term "pharmaceutically acceptable salt" denotes a salt that is suitable for and fulfils the requirements related to for instance safety, bioavailability and tolerability (see for instance P. H. Stahl et al. (eds.) Handbook of Pharmaceutical Salts, Publisher Helvetica Chimica Acta, Zurich, 2002).

The synthesis of hexyl 5-ALA ester is known in the art. It may e.g. be prepared as described in WO 96/28412, the entire contents of which are incorporated herein by reference. Briefly, hexyl 5-ALA ester may be prepared by reaction of 5-ALA with hexanol in the presence of a catalyst, e.g. an acid. Further, hexyl 5-ALA ester hydrochloride is commercially available, e.g. in the form of Hexvix® (e.g. Photocure ASA) or Cysview® (e.g. Photocure Inc.).

The hexyl 5-ALA ester for use in the invention is preferably in the form of a pharmaceutically acceptable salt. Such salts are preferably acid addition salts with pharmaceutically acceptable organic or inorganic acids. Suitable acids include, for example, hydrochloric, nitric, hydrobromic, phosphoric, sulfuric, sulfonic acid and sulfonic acid derivatives, the salts of ALA-esters and the latter acids are described in WO 2005/092838, the entire contents of which are incorporated herein by reference. A preferred acid is hydrochloride acid, HCl. Synthetic procedures for salt formation are conventional in the art and are for instance described in WO 2005/092838.

The concentration of HAL in the composition for use in the invention is conveniently in the range of 0.1 to 5% by weight of the total weight of the composition or the equivalent concentration of a pharmaceutically acceptable salt of HAL, preferably 0.15 to 3.5%, and most preferably 0.17%, which corresponds to e.g. 0.2% HAL hydrochloride (8 mM).

The composition for use in the invention may comprise pharmaceutically acceptable carriers, excipients, or stabilizers. The composition for use in the invention is preferably a liquid composition, more preferably a suspension or even more preferably a solution of HAL in a liquid carrier. Preferred liquid carriers are water or aqueous solutions, most preferred liquid carriers are aqueous buffers.

In a preferred embodiment, the composition for use in the invention is an aqueous solution of HAL and most preferably a solution of HAL in an aqueous buffer, preferably a phosphate buffer. In a particularly preferred embodiment, the composition for use in the invention comprises as a liquid carrier an aqueous phosphate buffer comprising disodium phosphate dehydrate, potassium dihydrogen phosphate, sodium chloride, hydrochloric acid, sodium hydroxide and water.

In a preferred embodiment, HAL or the pharmaceutically acceptable salt thereof is provided in a lyophilized form, and is reconstituted in a liquid carrier, preferably in water or an aqueous solution, most preferably in an aqueous buffer, prior to use.

If the composition for use in the invention is a liquid composition comprising water, the pH of said composition is preferably in the range of 4.5 to 7.5, more preferably a pH in the range of 5.7 to 7.2.

In a particularly preferred embodiment, the composition for use of the invention is Hexvix®, i.e. a solution of HAL hydrochloride (2 mg/ml; 8 mM) in an aqueous buffer comprising disodium phosphate dehydrate, potassium dihydrogen phosphate, sodium chloride, hydrochloric acid, sodium hydroxide and water.

The amount of the composition, which is instilled into the bladder, may vary according to the bladder volume and size. In general, and as observed in the use of Hexvix®, a volume of about 50 ml of the composition comprising 0.2% HAL hydrochloride (8 mM) is suitable and sufficient.

The composition for use in the invention is instilled preferably into the empty bladder through a catheter and is left in the bladder from about 20 minutes to about 3 hours, more preferably from about 30 minutes to about 2 hours, most preferably no less than about 1 hour. Prior to exposing the inside of the bladder to light, the bladder is evacuated. If the patient cannot retain the composition for about 1 hour, at least about 1 hour should be allowed to pass from the instillation of the composition into the bladder to the start of exposing the inside of the bladder to light.

In a preferred embodiment, Hexvix® is instilled into the bladder through a catheter and is left in the bladder for about 1 hour. The bladder is then evacuated, before the inside of the bladder is exposed to light. If the patient cannot retain the composition for about 1 hour, at least about 1 hour is allowed to pass from the instillation of Hexvix® to the start of exposing the inside of the bladder to light.

In the method of the invention, the inside of the bladder is exposed to blue light having a fluence rate of 1.5 to 12.5 mW/cm$^2$. In a preferred embodiment, the inside of the bladder is exposed to blue light having a fluence rate of 2.5 to 7.0 mW/cm$^2$, e.g. 5.5, 6.0 or 6.5 mW/cm$^2$ or 5.5 to 8.5 mW/cm$^2$, e.g. 6.0, 6.5. 7.0, 7.5 or 8.0 mW/cm$^2$.

In a preferred method of the invention, the inside of the bladder is exposed to blue light having a fluence rate of 1.5 to 12.5 mW/cm$^2$ and said blue light is provided at a light dose of 0.2 to 15 J/cm$^2$. In a more preferred embodiment, the inside of the bladder is exposed to blue light having a fluence rate of 1.5 to 12.5 mW/cm$^2$ and blue light is provided at a light dose of 0.3 to 8.0 J/cm$^2$, e.g. 6.5, 7.0 or 7.5 J/cm$^2$.

In yet another preferred embodiment, the inside of the bladder is exposed to blue light having a fluence rate of 2.5 to 7.0 mW/cm$^2$, e.g. 5.5, 6.0 or 6.5 mW/cm$^2$ or to blue light having a fluence rate of 5.5 to 8.5 mW/cm$^2$, e.g. 6.0, 6.5. 7.0, 7.5 or 8.0 mW/cm$^2$ and said blue light is provided at a light dose of 0.2 to 15 J/cm$^2$. In a more preferred embodiment, the inside of the bladder is exposed to blue light having a fluence rate of 2.5 to 7.0 mW/cm$^2$, e.g. 5.5, 6.0 or 6.5 mW/cm$^2$ or to blue light having a fluence rate of 5.5 to 8.5 mW/cm$^2$, e.g. 6.0, 6.5. 7.0, 7.5 or 8.0 mW/cm$^2$ and said blue light is provided at a light dose of 0.7 to 10.2 J/cm$^2$. In another more preferred embodiment, the inside of the bladder is exposed to blue light having a fluence rate of 2.5 to 7.0 mW/cm$^2$, e.g. 5.5, 6.0 or 6.5 mW/cm$^2$ or to blue light having a fluence rate of 5.5 to 8.5 mW/cm$^2$, e.g. 6.0, 6.5. 7.0, 7.5 or 8.0 mW/cm$^2$ and said blue light is provided at a light dose of 0.3 to 8.0 J/cm$^2$, e.g. 6.5, 7.0 or 7.5 J/cm$^2$.

In yet another preferred embodiment, the inside of the bladder is exposed to blue light having a fluence rate of 2.5 to 7.0 mW/cm$^2$, e.g. 5.5, 6.0 or 6.5 mW/cm$^2$ and said blue light is provided at a light dose of 0.3 to 8.0 J/cm$^2$, e.g. 6.5, 7.0 or 7.5 J/cm$^2$. In yet another preferred embodiment, the inside of the bladder is exposed to blue light having a fluence rate of 5.5 to 8.5 mW/cm$^2$, e.g. 6.0, 6.5. 7.0, 7.5 or 8.0 mW/cm$^2$ and said blue light is provided at a light dose of 0.7 to 10.2.0 J/cm$^2$.

In another embodiment, the invention provides a method of photodynamic therapy for bladder cancer, comprising the instillation into the bladder of a patient in need of such treatment of a composition comprising hexyl 5-ALA ester (HAL) or a pharmaceutically acceptable salt thereof, exposing the inside of said bladder to white light having a fluence rate of 3.0 to 22.0 mW/cm$^2$ and to blue light having a fluence rate of 1.5 to 12.5 mW/cm$^2$. In a preferred embodiment, the invention provides a method of photodynamic therapy for bladder cancer, comprising the instillation into the bladder of a patient in need of such treatment of a composition comprising hexyl 5-ALA ester (HAL) or a pharmaceutically acceptable salt thereof, exposing the inside of said bladder to white light having a fluence rate of 3.0 to 22.0 mW/cm$^2$ and to blue light having a fluence rate of 1.5 to 12.5 mW/cm$^2$, wherein said white light is provided at a light dose of 0.4 to 26.5 J/cm$^2$ and said blue light at light dose of 0.2 to 15 J/cm$^2$.

In an alternative embodiment, the invention provides a composition comprising hexyl 5-ALA ester (HAL) or a pharmaceutically acceptable salt thereof for use in a method of photodynamic therapy for bladder cancer, wherein said composition is instilled into the bladder of a patient in need of such treatment and the inside of said bladder is exposed to white light having a fluence rate of 3.0 to 22.0 mW/cm$^2$ and to blue light having a fluence rate of 1.5 to 12.5 mW/cm$^2$. In a preferred alternative embodiment, the invention provides a composition comprising hexyl 5-ALA ester (HAL) or a pharmaceutically acceptable salt thereof for use in a method of photodynamic therapy for bladder cancer, wherein said composition is instilled into the bladder of a patient in need of such treatment and the inside of said bladder is exposed to white light having a fluence rate of 3.0 to 22.0 mW/cm$^2$ and to blue light having a fluence rate of 1.5 to 12.5 mW/cm$^2$ and wherein said white light is provided at a light dose of 0.4 to 26.5 J/cm2 and said blue light is provided at light dose of 0.2 to 15 J/cm$^2$.

In a preferred embodiment, the inside of the bladder is exposed to white light having a fluence rate of 5.0 to 12.5 mW/cm$^2$, e.g. 7.0, 9.0 or 11.0 mW/cm$^2$, and to blue light having a fluence rate of 2.5 to 7.0 mW/cm$^2$, e.g. 5.5, 6.0 or 6.5 mW/cm$^2$.

In a further preferred embodiment, the inside of the bladder is exposed to white light having a fluence rate of 5.0 to 12.5 mW/cm$^2$, e.g. 7.0, 9.0 or 11.0 mW/cm$^2$, and to blue light having a fluence rate of 2.5 to 7.0 mW/cm$^2$, e.g. 5.5, 6.0 or 6.5 mW/cm$^2$, wherein said blue light is provided at light dose of 0.3 to 8.0 J/cm$^2$, e.g. 6.5, 7.0 or 7.5 J/cm$^2$ and said white light at a light dose of 0.6 to 15.0 J/cm$^2$, e.g. 10.0, 11.5 or 13.0 J/cm$^2$.

Generally, irradiation, i.e. exposure of the inside of the bladder to blue or white and blue light, is carried out for a period of 2 to 20 minutes.

For exposing the inside of the bladder to light, blue light, i.e. wavelengths of from about 360 nm to about 450 nm, is used. In another embodiment, white light, i.e. visible light with wavelengths of from about 350 to about 700 nm and blue light, i.e. wavelengths of from about 360 nm to about 450 nm, is used. For both blue light and white light exposure, the inside of the bladder may first be exposed to white light and then to blue light or vice versa. In a preferred embodiment, the inside of the bladder is first exposed to white light, then to blue light.

The light source may be a lamp or laser. In a preferred embodiment, a commercially available, rigid or flexible blue-light cystoscope (e.g. from Karl Storz, Olympus, Richard Wolf) is used in the method of photodynamic therapy of the invention as the light source. Such blue-light cystoscopes allow for both white and blue light irradiation, and no modifications such as light fibers or diffusing tips are needed to use such cystoscopes in the method of the invention. Commercially available cystoscopes are equipped with a lamp, e.g. a xenon arc lamp which emits white light and means to provide blue light, e.g. a filter system blocks all other wavelengths than those of blue light.

In a second embodiment, the invention provides a method of photodynamic therapy for bladder cancer, comprising the instillation into the bladder of a patient of a solution of HAL hydrochloride in an aqueous buffer, and exposing the inside of said bladder to blue light having a fluence rate of 1.5 to 12.5 mW/cm$^2$. In a preferred second embodiment, said blue light is provided at a light dose of 0.2 to 15.0 J/cm$^2$. In another preferred second embodiment, the inside of said bladder is exposed to white light having a fluence rate of 3.0 to 22.0 mW/cm$^2$ and to blue light having a fluence rate of 1.5 to 12.5 mW/cm$^2$. In yet another preferred second embodiment, the inside of said bladder is exposed to white light having a fluence rate of 3.0 to 22.0 mW/cm$^2$ and to blue light having a fluence rate of 1.5 to 12.5 mW/cm$^2$, wherein said white light is provided at a light dose of 0.4 to 26.5 J/cm$^2$ and said blue light at light dose of 0.2 to 15.0 J/cm$^2$.

In the second embodiment and in all the preferred second embodiments, the solution comprises 2 mg/ml HAL hydrochloride. Preferred fluence rates and/or light doses for blue light have been disclosed before and are preferably used in this second embodiment. Further, preferred fluence rates and/or light doses for white light have been disclosed before and are preferably used in this second embodiment. Also, preferred combinations of fluence rates and/or light doses for blue light and of fluence rates and/or light doses for white have been disclosed before and are preferably used in this second embodiment.

In a third embodiment, the invention provides a method of photodynamic therapy for bladder cancer, comprising the instillation into the bladder of a patient of a solution of HAL hydrochloride in an aqueous buffer, and exposing the inside of said bladder to blue light having a fluence rate of 2.5 to 7.0 mW/cm$^2$, e.g. 5.5, 6.0 or 6.5 mW/cm$^2$ or 5.5 to 8.5 mW/cm$^2$, e.g. 6.0, 6.5. 7.0, 7.5 or 8.0 mW/cm$^2$. In a preferred third embodiment, said blue light is provided at a light dose of 0.7 to 10.2 J/cm$^2$ or 0.3 to 8.0 J/cm$^2$, e.g. 6.5, 7.0 or 7.5 J/cm$^2$. In another preferred third embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$, e.g. 5.5, 6.0 or 6.5 mW/cm$^2$. In yet another preferred third embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$, e.g. 5.5, 6.0 or 6.5 mW/cm$^2$, wherein said white light is provided at a light dose of 0.6 to 15.0 J/cm$^2$, e.g. 10.0, 11.5 or 13.5 J/cm$^2$ and said blue light at light dose of 0.3 to 8.0 J/cm$^2$ e.g. 6.5, 7.0 or 7.5 J/cm$^2$.

In the third embodiment and in all the preferred third embodiments, the solution comprises 2 mg/ml HAL hydrochloride. Preferred fluence rates and/or light doses for blue light have been disclosed before and are preferably used in this third embodiment. Further, preferred fluence rates and/or light doses for white light have been disclosed before and are preferably used in this third embodiment. Also, preferred combinations of fluence rates and/or light doses for blue light and of fluence rates and/or light doses for white have been disclosed before and are preferably used in this third embodiment.

In a fourth embodiment, the invention provides a method of photodynamic therapy for bladder cancer, comprising the instillation into the bladder of a patient of a solution of HAL hydrochloride in an aqueous buffer comprising disodium phosphate dehydrate, potassium dihydrogen phosphate, sodium chloride, hydrochloric acid, sodium hydroxide and water, and exposing the inside of said bladder to blue light having a fluence rate of 1.5 to 12.5 mW/cm$^2$. In a preferred fourth embodiment, said blue light is provided at a light dose of 0.2 to 15.0 J/cm$^2$. In another preferred fourth embodiment, the inside of said bladder is exposed to white light having a fluence rate of 3.0 to 22.0 mW/cm$^2$ and to blue light having a fluence rate of 1.5 to 12.5 mW/cm$^2$. In yet another preferred fourth embodiment, the inside of said bladder is exposed to white light having a fluence rate of 3.0 to 22.0 mW/cm$^2$ and to blue light having a fluence rate of 1.5 to 12.5 mW/cm$^2$, wherein said white light is provided at a light dose of 0.4 to 26.5 J/cm$^2$ and said blue light at light dose of 0.2 to 15.0 J/cm$^2$.

In the fourth embodiment and in all the preferred fourth embodiments, the solution comprises 2 mg/ml HAL hydrochloride. Preferred fluence rates and/or light doses for blue light have been disclosed before and are preferably used in this fourth embodiment. Further, preferred fluence rates and/or light doses for white light have been disclosed before and are preferably used in this fourth embodiment. Also, preferred combinations of fluence rates and/or light doses for blue light and of fluence rates and/or light doses for white have been disclosed before and are preferably used in this fourth embodiment.

In a fifth embodiment, the invention provides a method of photodynamic therapy for bladder cancer, comprising the instillation into the bladder of a patient of a solution of HAL hydrochloride in an aqueous buffer comprising disodium phosphate dehydrate, potassium dihydrogen phosphate, sodium chloride, hydrochloric acid, sodium hydroxide and water, and exposing the inside of said bladder to blue light having a fluence rate of 2.5 to 7.0 mW/cm$^2$, e.g. 5.5, 6.0 or 6.5 mW/cm$^2$ or 5.5 to 8.5 mW/cm$^2$, e.g. 6.0, 6.5. 7.0, 7.5 or 8.0 mW/cm$^2$. In a preferred fifth embodiment, said blue light is provided at a light dose of 0.7 to 10.2 J/cm$^2$ or 0.3 to 8.0 J/cm$^2$, e.g. 6.5, 7.0 or 7.5 J/cm$^2$. In another preferred fifth embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$, e.g. 5.5, 6.0 or 6.5 mW/cm$^2$. In yet another preferred fifth embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$, e.g. 5.5, 6.0 or 6.5 mW/cm$^2$, wherein said white light is provided at a light dose of 0.6 to 15.0 J/cm$^2$, e.g. 10.0, 11.5 or 13.5 J/cm$^2$ and said blue light at light dose of 0.3 to 8.0 J/cm$^2$ e.g. 6.5, 7.0 or 7.5 J/cm$^2$.

In the fifth embodiment and in all the preferred fifth embodiments, the solution comprises 2 mg/ml HAL hydrochloride. Preferred fluence rates and/or light doses for blue light have been disclosed before and are preferably used in this fifth embodiment. Further, preferred fluence rates and/or light doses for white light have been disclosed before and are preferably used in this fifth embodiment. Also, preferred combinations of fluence rates and/or light doses for blue light and of fluence rates and/or light doses for white have been disclosed before and are preferably used in this fifth embodiment.

In a sixth embodiment, the invention provides a method of photodynamic therapy for bladder cancer, comprising the instillation into the bladder of a patient of a solution of HAL hydrochloride in an aqueous buffer, and exposing the inside of said bladder to blue light having a fluence rate of 1.5 to 12.5 mW/cm$^2$, wherein said blue light is provided at a light dose of 0.2 to 15.0 J/cm$^2$. In a preferred sixth embodiment, the inside of said bladder is exposed to white light having a fluence rate of 3.0 to 22.0 mW/cm$^2$ and to blue light having a fluence rate of 1.5 to 12.5 mW/cm$^2$, wherein said white light is provided at a light dose of 0.4 to 26.5 J/cm$^2$ and said blue light at light dose of 0.2 to 15.0 J/cm$^2$.

In the sixth embodiment and in the preferred sixth embodiment, the solution comprises 2 mg/ml HAL hydrochloride. Preferred fluence rates and/or light doses for blue light have been disclosed before and are preferably used in this sixth embodiment. Further, preferred fluence rates and/or light doses for white light have been disclosed before and are preferably used in this sixth embodiment. Also, preferred combinations of fluence rates and/or light doses for blue light and of fluence rates and/or light doses for white have been disclosed before and are preferably used in this sixth embodiment.

In a seventh embodiment, the invention provides a method of photodynamic therapy for bladder cancer, comprising the instillation into the bladder of a patient of a solution of HAL hydrochloride in an aqueous buffer, and exposing the inside of said bladder to blue light having a fluence rate of 2.5 to 7.0 mW/cm$^2$ e.g. 5.5, 6.0 or 6.5 mW/cm$^2$ or 5.5 to 8.5 mW/cm$^2$, e.g. 6.0, 6.5. 7.0, 7.5 or 8.0 mW/cm$^2$, wherein said blue light is provided at a light dose of 0.7 to 10.2 J/cm$^2$ or 0.3 to 8.0 J/cm$^2$, e.g. 6.5, 7.0 or 7.5 J/cm$^2$. In a preferred seventh embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$ e.g. 5.5, 6.0 or 6.5 mW/cm$^2$, wherein said white light is provided at a light dose of 0.6 to 15.0 J/cm$^2$, e.g. 10.0, 11.5 or 13.5 J/cm$^2$ and said blue light at light dose of 0.3 to 8.0 J/cm$^2$, e.g. 6.5, 7.0 or 7.5 J/cm$^2$.

In the seventh embodiment and in the preferred seventh embodiment, the solution comprises 2 mg/ml HAL hydrochloride. Preferred fluence rates and/or light doses for blue light have been disclosed before and are preferably used in this seventh embodiment. Further, preferred fluence rates and/or light doses for white light have been disclosed before and are preferably used in this seventh embodiment. Also, preferred combinations of fluence rates and/or light doses for blue light and of fluence rates and/or light doses for white have been disclosed before and are preferably used in this seventh embodiment.

In an eighth embodiment, the invention provides a method of photodynamic therapy for bladder cancer, comprising the instillation into the bladder of a patient of a solution of HAL hydrochloride in an aqueous buffer comprising disodium phosphate dehydrate, potassium dihydrogen phosphate, sodium chloride, hydrochloric acid, sodium hydroxide and water, and exposing the inside of said bladder to blue light having a fluence rate of 1.5 to 12.5 mW/cm$^2$, wherein said blue light is provided at a light dose of 0.2 to 15.0 J/cm$^2$. In a preferred eighth embodiment, the inside of said bladder is exposed to white light having a fluence rate of 3.0 to 22.0 mW/cm$^2$ and to blue light having a fluence rate of 1.5 to 12.5 mW/cm$^2$, wherein said white light is provided at a light dose of 0.4 to 26.5 J/cm$^2$ and said blue light at light dose of 0.2 to 15.0 J/cm$^2$.

In the eighth embodiment and in the preferred eighth embodiment, the solution comprises 2 mg/ml HAL hydrochloride. Preferred fluence rates and/or light doses for blue light have been disclosed before and are preferably used in this eighth embodiment. Further, preferred fluence rates and/or light doses for white light have been disclosed before and are preferably used in this eighth embodiment. Also, preferred combinations of fluence rates and/or light doses for blue light and of fluence rates and/or light doses for white have been disclosed before and are preferably used in this eighth embodiment.

In a ninth embodiment, the invention provides a method of photodynamic therapy for bladder cancer, comprising the instillation into the bladder of a patient of a solution of HAL hydrochloride in an aqueous buffer comprising disodium phosphate dehydrate, potassium dihydrogen phosphate, sodium chloride, hydrochloric acid, sodium hydroxide and water, and exposing the inside of said bladder to blue light having a fluence rate of 2.5 to 7.0 mW/cm$^2$ e.g. 5.5, 6.0 or 6.5 mW/cm$^2$ or 5.5 to 8.5 mW/cm$^2$, e.g. 6.0, 6.5. 7.0, 7.5 or 8.0 mW/cm$^2$, wherein said blue light is provided at a light dose of 0.7 to 10.2 J/cm$^2$ or 0.3 to 8.0 J/cm$^2$, e.g. 6.5, 7.0 or 7.5 J/cm$^2$. In a preferred ninth embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$ e.g. 5.5, 6.0 or 6.5 mW/cm$^2$, wherein said white light is provided at a light dose of 0.6 to 15.0 J/cm$^2$, e.g. 10.0, 11.5 or 13.5 J/cm$^2$ and said blue light at light dose of 0.3 to 8.0 J/cm$^2$, e.g. 6.5, 7.0 or 7.5 J/cm$^2$.

In the ninth embodiment and in the preferred ninth embodiment, the solution comprises 2 mg/ml HAL hydrochloride. Preferred fluence rates and/or light doses for blue light have been disclosed before and are preferably used in this ninth embodiment. Further, preferred fluence rates and/or light doses for white light have been disclosed before and are preferably used in this ninth embodiment. Also, preferred combinations of fluence rates and/or light doses for blue light and of fluence rates and/or light doses for white have been disclosed before and are preferably used in this ninth embodiment.

In said second to ninth embodiment, the light source is preferably a commercially available blue-light cystoscope which allows blue light irradiation or for blue and white light irradiation.

In said second to ninth embodiment, said solution of HAL hydrochloride is instilled into the bladder through a catheter and is preferably left in the bladder for about 1 hour. In a preferred second to ninth embodiment, the bladder is evacuated prior to exposing the inside of the bladder to light. If the patient cannot retain the said solution for about 1 hour, at least about 1 hour is allowed to pass from the instillation of the solution to the start of exposing the inside of the bladder to light.

The method of photodynamic therapy for bladder cancer according to the invention can be used as stand-alone bladder cancer treatment. Alternatively, it can be used as adjuvant therapy in the treatment of bladder cancer, i.e. in addition to a primary/main therapy for bladder cancer.

Hence, in a tenth embodiment, the invention provides a method of treating bladder cancer wherein a method of photodynamic therapy is used as adjuvant therapy, said method of photodynamic therapy comprises the instillation into the bladder of a patient of a composition comprising hexyl 5-ALA ester (HAL) or a pharmaceutically acceptable salt thereof, and exposing the inside of said bladder to blue light having a fluence rate of 1.5 to 12.5 mW/cm$^2$. In a preferred tenth embodiment, said blue light is provided at a light dose of 0.2 to 15.0 J/cm$^2$. In another preferred tenth embodiment, the inside of said bladder is exposed to white light having a fluence rate of 3.0 to 22.0 mW/cm$^2$ and to blue light having a fluence rate of 1.5 to 12.5 mW/cm$^2$. In yet another preferred tenth embodiment, the inside of said bladder is exposed to white light having a fluence rate of 3.0 to 22.0 mW/cm$^2$ and to blue light having a fluence rate of 1.5 to 12.5 mW/cm$^2$, wherein said white light is provided at a light dose of 0.4 to 26.5 J/cm$^2$ and said blue light at light dose of 0.2 to 15.0 J/cm$^2$.

In an eleventh embodiment, the invention provides a method of treating bladder cancer wherein a method of photodynamic therapy is used as adjuvant therapy, said method of photodynamic therapy comprises the instillation into the bladder of a patient of a composition comprising hexyl 5-ALA ester (HAL) or a pharmaceutically acceptable salt thereof, and exposing the inside of said bladder to blue light having a fluence rate of 2.5 to 7.0 mW/cm$^2$, e.g. 5.5, 6.0 or 6.5 mW/cm$^2$ or 5.5 to 8.5 mW/cm$^2$, e.g. 6.0, 6.5. 7.0, 7.5 or 8.0 mW/cm$^2$. In a preferred eleventh embodiment, said blue light is provided at a light dose of 0.7 to 10.2 J/cm$^2$ or 0.3 to 8.0 J/cm$^2$, e.g. 6.5, 7.0 or 7.5 J/cm$^2$. In another preferred eleventh embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$, e.g. 5.5, 6.0 or 6.5 mW/cm$^2$. In yet another preferred eleventh embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$, e.g. 5.5, 6.0 or 6.5 mW/cm$^2$, wherein said white light is provided at a light dose of 0.6 to 15.0 J/cm$^2$, e.g. 10.0, 11.5 or 13.5 J/cm$^2$ and said blue light at light dose of 0.3 to 8.0 J/cm$^2$ e.g. 6.5, 7.0 or 7.5 J/cm$^2$.

In an alternative tenth embodiment, the invention provides a composition comprising hexyl 5-ALA ester (HAL) or a pharmaceutically acceptable salt thereof for use in a method of treating bladder cancer wherein a method of photodynamic therapy is used as adjuvant therapy, said method of photodynamic therapy comprises the instillation of the composition into the bladder of a patient in need of such treatment and exposing the inside of said bladder to blue light having a fluence rate of 1.5 to 12.5 mW/cm$^2$. In a preferred alternative tenth embodiment, said blue light is provided at a light dose of 0.2 to 15.0 J/cm$^2$. In another preferred alternative tenth embodiment, the inside of said bladder is exposed to white light having a fluence rate of 3.0 to 22.0 mW/cm$^2$ and to blue light having a fluence rate of 1.5 to 12.5 mW/cm$^2$. In yet another preferred alternative tenth embodiment, the inside of said bladder is exposed to white light having a fluence rate of 3.0 to 22.0 mW/cm$^2$ and to blue light having a fluence rate of 1.5 to 12.5 mW/cm$^2$, wherein said white light is provided at a light dose of 0.4 to 26.5 J/cm$^2$ and said blue light at light dose of 0.2 to 15.0 J/cm$^2$.

In an alternative eleventh embodiment, the invention provides a composition comprising hexyl 5-ALA ester (HAL) or a pharmaceutically acceptable salt thereof for use in a method of treating bladder cancer wherein a method of photodynamic therapy is used as adjuvant therapy, said method of photodynamic therapy comprises the instillation of the composition into the bladder of a patient in need of such treatment and exposing the inside of said bladder to blue light having a fluence rate of 2.5 to 7.0 mW/cm$^2$, e.g. 5.5, 6.0 or 6.5 mW/cm$^2$ or 5.5 to 8.5 mW/cm$^2$, e.g. 6.0, 6.5. 7.0, 7.5 or 8.0 mW/cm$^2$. In a preferred alternative eleventh embodiment, said blue light is provided at a light dose of 0.7 to 10.2 J/cm$^2$ or 0.3 to 8.0 J/cm$^2$, e.g. 6.5, 7.0 or 7.5 J/cm$^2$. In another preferred alternative eleventh embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$, e.g. 5.5, 6.0 or 6.5 mW/cm$^2$. In yet another preferred alternative eleventh embodiment, the inside of said bladder is exposed to white light having a fluence rate of 5.0 to 12.5 mW/cm$^2$, e.g. 7.0, 9.0 or 11.0 mW/cm$^2$ and to blue light having a fluence rate of 2.5 to 7.0 mW/cm$^2$, e.g. 5.5, 6.0 or 6.5 mW/cm$^2$, wherein said white light is provided at a light dose of 0.6 to 15.0 J/cm$^2$, e.g. 10.0, 11.5 or 13.5 J/cm$^2$ and said blue light at light dose of 0.3 to 8.0 J/cm$^2$ e.g. 6.5, 7.0 or 7.5 J/cm$^2$.

In a preferred tenth or eleventh embodiment, or in a preferred alternative tenth or eleventh embodiment, the composition for use in the method is an aqueous solution of HAL and most preferably a solution of HAL in an aqueous buffer, preferably a phosphate buffer. In a particularly preferred embodiment, the composition for use in the method comprises as a liquid carrier an aqueous phosphate buffer comprising disodium phosphate dehydrate, potassium dihydrogen phosphate, sodium chloride, hydrochloric acid, sodium hydroxide and water.

The bladder cancer in said tenth or eleventh embodiment, or in said preferred alternative tenth or eleventh embodiment may be NMIBC or MIBC.

Usually, for NMIBC, the main treatment is TUR, i.e. a procedure where the bladder is visualized through the urethra and tumors and lesions are resected. TUR is often followed by immune- and/or chemotherapy.

The method of photodynamic therapy of the invention is preferably carried out as adjuvant therapy to TUR in patients who are in need of such treatment, i.e. patients who have been diagnosed with NMIBC or in patients who are suspected to have NMIBC.

The adjuvant therapy of the invention may be carried out simultaneously with the TUR or after a TUR.

When carried out simultaneously, a method of treating NMIBC thus may commence with the instillation into the bladder of a patient in need of such treatment of a composition comprising hexyl 5-ALA ester (HAL) or a pharmaceutically acceptable salt thereof, and exposing the inside of said bladder to white light for a visual inspection and then switching to blue light for fluorescence detection and treatment of lesions. Said lesions are then resected, e.g. under white light. The completeness of the resection may be monitored by use of blue light. In the said method, the inside of the bladder is exposed to blue light having a fluence rate of 1.5 to 12.5 mW/cm$^2$. In a preferred embodiment, said aforementioned white light has a fluence rate of 3.0 to 22.0 mW/cm$^2$. In a preferred embodiment, said aforementioned blue light is provided at a light dose of 0.2 to 15.0 J/cm$^2$. In a further preferred embodiment, said aforementioned white light is provided at a light dose of 0.4 to 26.5 J/cm$^2$. The irradiation/the light exposure is carried out for a period of 2 (for small and/or few lesions) to 20 minutes (for large and/or multiple lesions).

Thus, in an twelfth embodiment, the invention provides a method of treating NMIBC by simultaneously carrying out an adjuvant therapy and a transurethral resection of NMIBC, said method comprises a) instillation of a composition comprising hexyl 5-ALA ester (HAL) or a pharmaceutically acceptable salt thereof into the bladder of a patient in need of such NMIBC treatment, b) exposing the inside of said bladder to white light for a visual inspection followed by exposing said inside to blue light for fluorescence detection and treatment of lesions; c) resection of said lesions; and d) optionally monitoring the completeness of the resection by exposing said inside to blue light for fluorescence detection of residual NMIBC, wherein the blue light has a fluence rate of 1.5 to 12.5 mW/cm$^2$.

In a preferred twelfth embodiment, said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

In a further preferred twelfth embodiment, the invention provides a method of treating NMIBC by simultaneously carrying out an adjuvant therapy and a transurethral resection of NMIBC, said method comprises a) instillation of a composition comprising hexyl 5-ALA ester (HAL) or a pharmaceutically acceptable salt thereof into the bladder of a patient in need of such NMIBC treatment, b) exposing the inside of said bladder to white light for a visual inspection followed by exposing said inside to blue light for fluorescence detection and treatment of lesions; c) resection of said lesions; and d) optionally monitoring the completeness of the resection by exposing said inside to blue light for fluorescence detection of residual NMIBC, wherein the white light has a fluence rate of 3.0 to 22.0 mW/cm$^2$ and the blue light has a fluence rate of 1.5 to 12.5 mW/cm$^2$.

In yet a further preferred twelfth embodiment, said white light is provided at a light dose of 0.4 to 26.5 J/cm$^2$ and said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

Various embodiments and preferred embodiments of the method of treating NMIBC, i.e. embodiments 1-11, are described above and can be used in this twelfth embodiment.

In an alternative twelfth embodiment, the invention provides a composition comprising hexyl 5-ALA ester (HAL) or a pharmaceutically acceptable salt thereof for use in a method of treating NMIBC by simultaneously carrying out an adjuvant therapy and a transurethral resection of NMIBC, wherein a) said composition is instilled into the bladder of a patient in need of such NMIBC treatment, b) the inside of said bladder is exposed to white light for a visual inspection followed by exposing said inside to blue light for fluorescence detection and treatment of lesions; c) said lesions are resected; and d) optionally the completeness of the resection is monitored by exposing said inside to blue light for fluorescence detection of residual NMIBC, wherein the blue light has a fluence rate of 1.5 to 12.5 mW/cm$^2$.

In a preferred alternative twelfth embodiment, said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

In a further preferred alternative twelfth embodiment, the invention provides a composition comprising hexyl 5-ALA ester (HAL) or a pharmaceutically acceptable salt thereof for use in a method of treating NMIBC a method of treating NMIBC by simultaneously carrying out an adjuvant therapy and a transurethral resection of NMIBC, wherein a) said composition is instilled into the bladder of a patient in need of such NMIBC treatment, b) the inside of said bladder is exposed to white light for a visual inspection followed by exposing said inside to blue light for fluorescence detection and treatment of lesions; c) said lesions are resected; and d) optionally the completeness of the resection is monitored by exposing said inside to blue light for fluorescence detection of residual NMIBC, wherein the white light has a fluence rate of 3.0 to 22.0 mW/cm$^2$ and the blue light has a fluence rate of 1.5 to 12.5 mW/cm$^2$.

In yet a further preferred twelfth embodiment, said white light is provided at a light dose of 0.4 to 26.5 J/cm$^2$ and said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

Various embodiments and preferred embodiments of the composition comprising hexyl 5-ALA ester (HAL) or a pharmaceutically acceptable salt thereof for use in a method of treating NMIBC, i.e. embodiments 1-11, are described above and can be used in this alternative twelfth embodiment.

When carried out after a TUR, the adjuvant therapy for treating NMIBC may commence with the instillation into the bladder of a patient having undergone TUR of a composition comprising hexyl 5-ALA ester (HAL) or a pharmaceutically acceptable salt thereof and exposing the inside of said bladder to blue light having a fluence rate of 1.5 to 12.5 mW/cm$^2$.

Thus, in a thirteenth embodiment, the invention provides an adjuvant therapy for treating NMIBC, comprising instillation of a composition comprising hexyl 5-ALA ester (HAL) or a pharmaceutically acceptable salt thereof into the bladder of a patient having undergone TUR and exposing the inside of said bladder to blue light having a fluence rate of 1.5 to 12.5 mW/cm$^2$.

In a preferred thirteenth embodiment, said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

In a further preferred thirteenth embodiment, the invention provides an adjuvant therapy for treating NMIBC, comprising instillation of a composition comprising hexyl 5-ALA ester (HAL) or a pharmaceutically acceptable salt thereof into the bladder of a patient having undergone TUR and exposing the inside of said bladder to white light having a fluence rate of 3.0 to 22.0 mW/cm$^2$ and to blue light having a fluence rate of 1.5 to 12.5 mW/cm$^2$.

In yet a further preferred thirteenth embodiment, said white light is provided at a light dose of 0.4 to 26.5 J/cm$^2$ and said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

Various embodiments and preferred embodiments of the method of treating NMIBC, i.e. embodiments 1-11, are described above and can be used in this thirteenth embodiment.

In an alternative thirteenth embodiment, the invention provides a composition comprising hexyl 5-ALA ester (HAL) or a pharmaceutically acceptable salt thereof for use in an adjuvant therapy for treating NMIBC, wherein said composition is instilled into the bladder of a patient who has undergone TUR and the inside of said bladder is exposed to blue light having a fluence rate of 1.5 to 12.5 mW/cm$^2$.

In a preferred alternative thirteenth embodiment, said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

In a further preferred alternative thirteenth embodiment, the invention provides a composition comprising hexyl 5-ALA ester (HAL) or a pharmaceutically acceptable salt thereof for use in an adjuvant therapy for treating NMIBC, wherein said composition is instilled into the bladder of a patient having undergone TUR and the inside of said bladder is exposed to white light having a fluence rate of 3.0 to 22.0 mW/cm$^2$ and to blue light having a fluence rate of 1.5 to 12.5 mW/cm$^2$.

In yet a further preferred alternative thirteenth embodiment, said white light is provided at a light dose of 0.4 to 26.5 J/cm$^2$ and said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

Various embodiments and preferred embodiments of the composition comprising hexyl 5-ALA ester (HAL) or a pharmaceutically acceptable salt thereof for use in this adjuvant therapy for NMIBC, i.e. embodiments 1-11, are described above and can be used in this alternative thirteenth embodiment.

The method of treating NMIBC according to the invention may be carried out once or repeatedly, e.g. two or more times, e.g. 3, 4, 5 or 6 times, with a period between the treatments of e.g. 4 days to 4 weeks, e.g. 1, 2 or 3 weeks.

The adjuvant therapy for NMIBC according to the invention may be carried out once or repeatedly, e.g. two or more times, e.g. 3, 4, 5 or 6 times, with a period between the treatments of e.g. 4 days to 4 weeks, e.g. 1, 2 or 3 weeks, either together with a TUR, e.g. after a TUR, or alone.

The adjuvant therapy for treating NMIBC of the invention can be used in combination with chemotherapy, e.g. systemic or intravesical administration of suitable chemotherapeutic agents for NMIBC, such as cisplatin, methotrexate, vinblastine, valrubicin, adriamycin or mitomycin C and/or in combination with suitable immunotherapeutic agents for NMIBC, such as systemic administration of anticancer vaccines or intravesical administration of Bacillus Calmette-Guérin (BCG).

Alternatively, the adjuvant therapy for treating NMIBC according to the invention may replace or partially replace other adjuvant therapies like chemotherapy and/or immunotherapy. In a preferred embodiment, the adjuvant therapy according to the invention replaces or partially replaces other adjuvant therapies which are intravesically administered, e.g. mitomycin and/or BCG. In a particularly preferred embodiment, the adjuvant therapy for treating NMIBC according to the invention partially or fully replaces BCG. BCG treatment is usually started a few weeks after a transurethral resection of NMIBC and is given once a week for 6 weeks. The adjuvant therapy according to the invention may replace 1, 2, 3, 4, 5 or all 6 of such BCG treatments.

Up to 40% of patients with NMIBC will fail intravesical BCG therapy. The vast majority of low-grade NMIBC are prone to recur but very rarely progress. Failure after intravesical BCG in these patients is usually superficial and low-grade, and such patients can be managed with intravesical regimens, including repeated BCG, BCG plus cytokines, intravesical chemotherapy, thermochemotherapy or new immunotherapeutic modalities. At the other end of the spectrum, failure to respond to BCG in high-risk T1 bladder cancer and/or carcinoma in situ is more problematic, since those tumors often have the potential to progress to muscle invasion. In these cases, radical cystectomy remains the mainstay after BCG failure. Hence there is a need to find new therapeutic alternatives for BCG refractory bladder cancer patients and the adjuvant therapy for treating NMIBC according to the invention meets this need.

Full replacement of BCG by the adjuvant therapy according to the invention is preferably used in BCG refractory NMIBC patients, i.e. patients where BCG therapy does not lead to the desired treatment success.

Hence, in a fourteenth embodiment the invention provides a adjuvant therapy for treating NMIBC in BCG refractory patients, comprising installation of a composition comprising hexyl 5-ALA ester (HAL) or a pharmaceutically acceptable salt thereof into the bladder of a BCG refractory patient and exposing the inside of said bladder to blue light having a fluence rate of 1.5 to 12.5 mW/cm$^2$.

In a preferred fourteenth embodiment, said blue light is provided at a light dose of 0.2 to 15.0 J/cm$^2$. Preferably, the irradiation/the light exposure is carried out for a period of 2 (for small and/or few lesions) to 20 minutes (for large and/or multiple lesions).

In a further preferred fourteenth embodiment, the invention provides an adjuvant therapy for treating NMIBC in BCG refractory patients, comprising instillation of a composition comprising hexyl 5-ALA ester (HAL) or a pharmaceutically acceptable salt thereof into the bladder of a BCG refractory patient and exposing the inside of said bladder to white light having a fluence rate of 3.0 to 22.0 mW/cm² and to blue light having a fluence rate of 1.5 to 12.5 mW/cm².

In yet a further preferred fourteenth embodiment, said white light is provided at a light dose of 0.4 to 26.5 J/cm² and said blue light is provided at a light dose of 0.2 to 15.0 J/cm². Preferably, the irradiation/the light exposure is carried out for a period of 2 (for small and/or few lesions) to 20 minutes (for large and/or multiple lesions).

Various embodiments and preferred embodiments of adjuvant therapy for treating NMIBC in BCG refractory patients, i.e. embodiments 1-11, are described above and can be used in this fourteenth embodiment.

In an alternative fourteenth embodiment, the invention provides a composition comprising hexyl 5-ALA ester (HAL) or a pharmaceutically acceptable salt thereof for use in an adjuvant therapy for treating NMIBC in BCG refractory patients, wherein said composition is instilled into the bladder of a BCG refractory patient and the inside of said bladder is exposed to blue light having a fluence rate of 1.5 to 12.5 mW/cm².

In a preferred alternative fourteenth embodiment, said blue light is provided at a light dose of 0.2 to 15.0 J/cm². Preferably, the irradiation/the light exposure is carried out for a period of 2 (for small and/or few lesions) to 20 minutes (for large and/or multiple lesions).

In a further preferred alternative fourteenth embodiment, the invention provides a composition comprising hexyl 5-ALA ester (HAL) or a pharmaceutically acceptable salt thereof for use in an adjuvant therapy for treating NMIBC in BCG refractory patients, wherein said composition is instilled into the bladder of a BCG refractory patient and the inside of said bladder is exposed to white light having a fluence rate of 3.0 to 22.0 mW/cm² and to blue light having a fluence rate of 1.5 to 12.5 mW/cm².

In yet a further preferred alternative fourteenth embodiment, said white light is provided at a light dose of 0.4 to 26.5 J/cm² and said blue light is provided at a light dose of 0.2 to 15.0 J/cm². Preferably, the irradiation/the light exposure is carried out for a period of 2 (for small and/or few lesions) to 20 minutes (for large and/or multiple lesions).

Various embodiments and preferred embodiments of the composition comprising hexyl 5-ALA ester (HAL) or a pharmaceutically acceptable salt thereof for use in this adjuvant therapy for treating NMIBC in BCG refractory patients, i.e. embodiments 1-11, are described above and can be used in this preferred alternative fourteenth embodiment.

For patients with MIBC, the main treatment is radical cystectomy, i.e. removal of the bladder and adjacent organs, i.e. prostate and seminal vesicles in men, and uterus and adnexa in women, including the dissection of regional lymph nodes. Cystectomy is also advocated in patients with NMIBC who are at high risk of progression, i.e. patients having multiple recurrent high-grade tumors or high-grade T1 tumors or high-grade tumors with concurrent carcinoma-in-situ (CIS). Further, cystectomy is advocated in patients with NMIBC who have received BCG immunotherapy but where such treatment has failed.

The method of photodynamic therapy of the invention is preferably carried out as a neoadjuvant therapy to cystectomy, i.e. prior to such a cystectomy, in patients who are in need of such treatment, i.e. patients who have been diagnosed with MIBC.

Thus, in a fifteenth embodiment, the invention provides a method of neoadjuvant therapy for treating MIBC prior to a cystectomy, said method comprising a) instillation into the bladder of a patient in need of said treatment of a composition comprising hexyl 5-ALA ester (HAL) or a pharmaceutically acceptable salt thereof; and b) exposing the inside of said bladder to blue light having a fluence rate of 1.5 to 12.5 mW/cm².

In a preferred fifteenth embodiment, said blue light is provided at a light dose of 0.2 to 15.0 J/cm². In another preferred fifteenth embodiment, the inside of said bladder is exposed to white light having a fluence rate of 3.0 to 22.0 mW/cm² and to blue light having a fluence rate of 1.5 to 12.5 mW/cm². In yet another preferred fifteenth embodiment, the inside of said bladder is exposed to white light having a fluence rate of 3.0 to 22.0 mW/cm² and to blue light having a fluence rate of 1.5 to 12.5 mW/cm², wherein said white light is provided at a light dose of 0.4 to 26.5 J/cm² and said blue light at light dose of 0.2 to 15.0 J/cm².

Various embodiments and preferred embodiments of this method of neoadjuvant therapy for treating MIBC, i.e. embodiments 1-11, are described above and can be used in this fifteenth embodiment.

In an alternative fourteenth embodiment, the invention provides a composition comprising hexyl 5-ALA ester (HAL) or a pharmaceutically acceptable salt thereof for use in a method of neoadjuvant therapy for treating MIBC, said method comprises a) instillation of the composition into the bladder of a patient in need of said treatment; and b) exposing the inside of said bladder to blue light having a fluence rate of 1.5 to 12.5 mW/cm²;

In a preferred alternative fifteenth embodiment, said blue light is provided at a light dose of 0.2 to 15.0 J/cm². In another preferred alternative fifteenth embodiment, the inside of said bladder is exposed to white light having a fluence rate of 3.0 to 22.0 mW/cm² and to blue light having a fluence rate of 1.5 to 12.5 mW/cm². In yet another preferred alternative fifteenth embodiment, the inside of said bladder is exposed to white light having a fluence rate of 3.0 to 22.0 mW/cm² and to blue light having a fluence rate of 1.5 to 12.5 mW/cm², wherein said white light is provided at a light dose of 0.4 to 26.5 J/cm² and said blue light at light dose of 0.2 to 15.0 J/cm².

Various embodiments and preferred embodiments of the composition comprising hexyl 5-ALA ester (HAL) or a pharmaceutically acceptable salt thereof for use in a method of neoadjuvant therapy for treating MIBC, i.e. embodiments 1-11, are described above and can be used in this alternative fifteenth embodiment.

In a sixteenth embodiment, the invention provides a method of treating MIBC, said method comprising a) neo-adjuvant therapy and b) a subsequent cystectomy, the method of treating MIBC comprising a) instillation into the bladder of a patient in need of said treatment of a composition comprising hexyl 5-ALA ester (HAL) or a pharmaceutically acceptable salt thereof and exposing the inside of said bladder to blue light having a fluence rate of 1.5 to 12.5 mW/cm²; and b) carrying out a cystectomy.

In a preferred sixteenth embodiment, said blue light is provided at a light dose of 0.2 to 15.0 J/cm². In another preferred sixteenth embodiment, the inside of said bladder is exposed to white light having a fluence rate of 3.0 to 22.0 mW/cm² and to blue light having a fluence rate of 1.5 to 12.5 mW/cm². In yet another preferred fifteenth embodiment, the inside of said bladder is exposed to white light having a fluence rate of 3.0 to 22.0 mW/cm² and to blue light having a fluence rate of 1.5 to 12.5 mW/cm², wherein said white light is provided at a light dose of 0.4 to 26.5 J/cm² and said blue light at light dose of 0.2 to 15.0 J/cm².

Various embodiments and preferred embodiments of this method of treating MIBC, i.e. embodiments 1-11, are described above and can be used in this sixteenth embodiment.

In an alternative sixteenth embodiment, the invention provides a composition comprising hexyl 5-ALA ester (HAL) or a pharmaceutically acceptable salt thereof for use in a method of treating MIBC, said method comprising a) neoadjuvant therapy and b) a subsequent cystectomy, the method of treating MIBC comprising a) instillation of the composition into the bladder of a patient in need of said treatment and exposing the inside of said bladder to blue light having a fluence rate of 1.5 to 12.5 mW/cm$^2$; and b) carrying out a cystectomy.

In a preferred alternative sixteenth embodiment, said blue light is provided at a light dose of 0.2 to 15.0 J/cm$^2$. In another preferred sixteenth embodiment, the inside of said bladder is exposed to white light having a fluence rate of 3.0 to 22.0 mW/cm$^2$ and to blue light having a fluence rate of 1.5 to 12.5 mW/cm$^2$. In yet another preferred fifteenth embodiment, the inside of said bladder is exposed to white light having a fluence rate of 3.0 to 22.0 mW/cm$^2$ and to blue light having a fluence rate of 1.5 to 12.5 mW/cm$^2$, wherein said white light is provided at a light dose of 0.4 to 26.5 J/cm$^2$ and said blue light at light dose of 0.2 to 15.0 J/cm$^2$.

Various embodiments and preferred embodiments of the composition comprising hexyl 5-ALA ester (HAL) or a pharmaceutically acceptable salt thereof for use in this method of treating MIBC, i.e. embodiments 1-11, are described above and can be used in this alternative sixteenth embodiment.

The time period between the neoadjuvant therapy of the invention described above and the cystectomy may vary but is preferably zero to 6 weeks, e.g. zero to 4, 3, 2 or 1 week. "Zero" means that the cystectomy is carried out directly after the neoadjuvant therapy, i.e. after the light irradiation/light exposure of the inside of the bladder is finalized.

The neoadjuvant therapy can be carried out repeatedly prior to the cystectomy, e.g. two or more times, e.g. 3, 4, 5 or 6 times, with a period between the treatments of e.g. 4 days to 4 weeks, e.g. 1, 2 or 3 weeks.

The neoadjuvant therapy can be carried out in combination with neoadjuvant radiotherapy and/or neoadjuvant chemotherapy.

Although being the gold standard for MIBC treatment and advocated in patients with certain types of NMIBC, radical cystectomy only provides 5-year survival in about 50% of patients. In order to improve these unsatisfactory results, the use of neoadjuvant therapies has been explored since the 1980s.

Neoadjuvant radiotherapy has been used, down staging of the cancer after radiotherapy takes about 4-6 weeks. However, a delay of surgery in patients with locally advanced bladder cancer beyond 90 days has shown to cause a significant increase in extravesical disease (81 vs 52%). Neoadjuvant radiotherapy is not recommended according to the current European guidelines on MIBC since no data exist to support that neoadjuvant radiotherapy for operable MIBC increases survival.

Neoadjuvant chemotherapy has many advantages including that chemotherapy is delivered at the earliest time-point, when the burden of micrometastatic disease is expected to be low; that tolerability of chemotherapy is expected to be better before cystectomy rather than after; and that hypothetically patients with micrometastatic disease might respond to neoadjuvant therapy and reveal favorable pathological status determined mainly by negative lymph node status and negative surgical margins. Neoadjuvant cisplatin-containing chemotherapy has shown to significantly improve survival (5% absolute improvement in survival at 5 years). However, as stated above, delayed cystectomy may compromise the outcome in patients who are not sensitive to chemotherapy and generally, pre-operative anemia and neuropathy is more common in patients receiving neoadjuvant chemotherapy prior to cystectomy. The current European guidelines on MIBC state that " . . . neoadjuvant chemotherapy has its limitations regarding patient selection, current development of surgical technique, and current chemotherapy combinations." Hence, there is room for improvement of neoadjuvant therapies for bladder cancer patients who need to undergo cystectomy.

The adjuvant or neoadjuvant therapies according to the method of the invention have several advantages compared to neoadjuvant radiotherapy, (neo)adjuvant chemotherapy and (neo)adjuvant immunotherapy, where nausea, vomiting, fatigue, anemia, damage to epithelial surfaces, intestinal discomfort/gastrointestinal stress, nephrotoxicity, neurotoxicity, swelling, depression of the immune system and infertility are well-known and common adverse effects. In contrary thereto, the most reported adverse reactions to HAL (in the form of Hexvix®/Cysview®) were transient and mild to moderate in intensity. The most frequently reported adverse reactions from clinical studies with Hexvix®/Cysview® were bladder spasm, reported by 2.4% of the patients, dysuria by 1.8%, bladder pain by 1.7% and hematuria by 1.7% of the patients.

In addition, HAL has a highly favorable metabolic profile compared to chemotherapeutics, e.g. cisplatin. HAL interferes with the body's own heme biosynthetic pathway and leads of accumulation of photoactive porphyrins, particularly protoporphyrin IX (PpIX), which is the last intermediate in heme synthesis. Since such photoactive porphyrins are compounds which naturally occur in the body, there is a "natural process" in the body for degrading (metabolizing) and excreting degraded heme.

EXAMPLES

Example 1

Orthotopic Rat Bladder Tumor Model

A rat bladder carcinoma cell line was used in these experiments to establish superficial bladder tumors in Female Fischer rats weighing 150-175 g as described in Francois, et al., J. Urol. 190(2), 2013, 731-736. The animals were used in the experiments 5 days after tumor cell inoculation.

PDT in Rat Bladders

Lyophilized HAL (in the form of Hexvix® powder) was dissolved in PBS to a final concentration of 2 mg/ml (8 mM). 0.5 ml of the solution was instilled into the rat bladder and was left in the bladder for about 1 hour. After evacuation of the HAL solution, 0.5 ml of PBS was instilled into the bladder and whole bladder irradiation with blue light at a fluence rate of 3.5 or 7.0 mW/cm$^2$ was performed using a 170 mW Modulight laser model ML 6500-405 delivering light at a wavelength of 401 nm, coupled to a fiber with a cylindrical diffuser (1×5 mm) model RD05/500/800 (Medlight, Ecublens, Switzerland) placed in a central position in the bladder. Rats received a blue light dose of 4.0 J/cm$^2$ (fluence rate 3.5 mW/cm$^2$) or 7.5 J/cm$^2$ (fluence rate 7.0 mW/cm$^2$)

For control, no Hexvix was instilled and only blue light irradiation was carried out at the aforementioned fluence rates/light doses.

Post PDT Protocol

The rats were sacrificed 48 hours after illumination by an overdose of pentobarbital. Bladders were filled in with formaldehyde (4%), removed from the animals and transferred into a vials with formaldehyde (4%) for a minimum of 4 h. Then the bladder was macroscopically cut into 4 parts and fixed for 48 h. Following different cycles of dehydration with gradients of ethanol and xylene, the bladder tissue was included into paraffin. Paraffin embedded sections of 5 μm were cut and used for histology with haematoxylin/eosin staining.

Results

Bladders of animals in the control group (n=2 for each fluence rate/light dose) showed no inflammation (sign of a PDT effect) but persistent and chorion infiltrating tumors for both fluence rates/light doses.

The bladders of 1 animal (50%) in the 3.5 mW/cm$^2$/4 J/cm$^2$ group (n=2) showed no inflammation, persistent and chorion infiltrating tumors while the tumor in the bladder of another animal (50%) looked less compact and the superficial layer of said tumor was destroyed.

Bladders of animals in the 7.0 mW/cm$^2$/7.5 J/cm$^2$ group (n=2) showed increased tissue thickness/inflammation (both signs of PDT effect) and disintegrating/less compact tumor tissue.

Example 2

HAL/Blue Light Group:

A solution of HAL (Hexvix®) was instilled into the bladder of patients through a catheter and was left in the bladder for about 1 hour. If the patient could not retain the composition for about 1 hour, at least about 1 hour was allowed to pass from the instillation of Hexvix® to the start of exposing the inside of the bladder to light. After evacuation of Hexvix®, a commercially available blue-light cystoscope was inserted into the bladder and a TUR was carried out by exposing the inside of the bladder to white light for the visual inspection, subsequent blue light exposure for fluorescence detection of bladder cancer lesions, resection of the detected lesions under white light and monitoring of the completeness of the resection by use of blue light. Blue light was provided at a fluence rate of 1.5 to 12.5 mW/cm$^2$ and a light dose of 0.2 to 15.0 J/cm$^2$ while light was provided at a fluence rate of 3.0 to 22.0 mW/cm$^2$ and a light dose of 0.4 to 26.5 J/cm$^2$.

The resected bladder tumors were processed according to methods known in the art and primary cell cultures were established from said patient-derived bladder tumor under appropriate conditions in culture medium. No in vitro primary cell cultures could be established from said resected bladder tumors.

No HAL/White Light Group:

A commercially available white light cystoscope was inserted into the bladder of patients and a TUR was carried out by exposing the inside of the bladder to white light for the visual inspection, detection of bladder cancer lesions, resection of said lesions and monitoring of the completeness of the resection.

Resected bladder tumors were processed identically to those in the HAL/blue light group. In vitro primary cell cultures of such resected bladder tumors could be established.

The fact that no in vitro primary cell cultures could be established from resected bladder tumors in the HAL/blue light patient group points towards a phototoxic effect, i.e. that tumor cells were killed in the applied TUR procedure.

Example 3

A prospective, randomized, comparative, controlled phase III multicenter study was carried out in patients with non-muscle invasive papillary bladder cancer (NMIBC). The study population comprised 551 patients which were randomized into two groups (see below). The groups were similar in age, gender, race, bladder cancer history and prior intravesical therapy.

HAL group: 271 patients. The method of the invention was carried out as follows: A solution of HAL (Hexvix®) was instilled into the bladder of patients through a catheter and was left in the bladder for about 1 hour. If the patient could not retain the composition for about 1 hour, at least about 1 hour was allowed to pass from the instillation of Hexvix® to the start of exposing the inside of the bladder to light.

After evacuation of Hexvix®, cystoscopy was carried out with a commercially available cystoscope (blue and white light). The inside of the bladder was first exposed to white light and visually assessed, followed by exposure to blue light to detect cancerous lesions in the bladder. Transurethral resection (TUR) of the detected lesions was carried out under white light and completion of the resection was assessed under blue light.

White light group: 280 patients. Cystoscopy and TUR of bladder cancer under white light only, no HAL.

Patients from both groups with histologically confirmed Ta or T1 lesions were followed up by white light cystoscopy after 3, 6 and 9 months. All tumor recurrences during the 9 months follow-up period were histologically confirmed.

Comparison of Tumor Recurrence in Patients in the White Light Group and the HAL Group According to the Invention Tumor recurrence was observed during the 9 months follow-up period in 157 of the 280 patients in the white light group (56.1%) and in 128 of 271 patients in the HAL group (42.7%). This difference in tumor recurrence rate is statistically significant and has been explained with improved tumor detection and more complete resection in the HAL group (Stenzl et al., J Urol 184, 2010, 1907-1914).

Comparison of Tumor Recurrence in Patients Who Did/ Did not Receive BCG Intravesical Treatment 50 patients in the HAL group (18.5%) and 55 patients in the white light group (19.6%) received BCG treatment during the 9 months follow-up period. BCG (Bacillus Calmette-Guérin) is an immunotherapy agent for the treatment of bladder cancer. It is usually repeatedly instilled into the bladder. Tumor recurrence rate in both patient groups were determined and the results are displayed in Table 1

TABLE 1

Tumor recurrence rate by group and BCG treatment

| Group | No BCG | Received BCG | All |
|---|---|---|---|
| White light (n = 280) | 61.8% (139/225) | 32.7% (18/55) | 56.1% (157/280) |
| HAL (n = 271) | 49.3% (109/221) | 38.0% (19/50) | 47.2% (128/271) |

As mentioned above, during the 9 months follow-up period in 157 of the 280 patients in the white light group (56.1%) and in 128 of 271 patients in the HAL group (42.7%) had confirmed tumor recurrence (Table 1, right column). This difference is mainly driven by the patients who did not receive BCG (61.8% in the white light group versus 49.3% in the HAL group). The difference in tumor recurrence for patients who received BCG between the groups is much less pronounced (32.7% in the white light group versus 38.0% in the HAL group)

In the white light group the difference in recurrence rate between the patients who received and who did not receive BCG treatment was statistically significant with a p-value <0.001 (32.7% versus 61.8%) which demonstrates the efficacy of BCG in preventing bladder cancer recurrence.

In the HAL group, however, the efficacy of BCG treatment could not be demonstrated, since the difference in recurrence rate between the patients who received and who did not receive BCG was not statistically significant (p-value=0.148, 38.0% versus 49.3%). This absence of significant BCG effect is mainly due to pronounced reduced tumor recurrence rate in patients wo did not receive BCG (49.3% versus 61.8%) and this reduction in tumor recurrence rate could possibly be explained by a therapeutic effect of HAL (HAL PDT effect) which results in the prevention of bladder cancer recurrence.

Comparison of Tumor Recurrence Rate in Patients Who Did/Did not Receive BCG and/or Mitomycin Intravesical Treatment Mitomycin is a chemotherapeutic agent for the treatment of bladder cancer. It may be instilled after TUR (single instillation) to e.g. prevent tumor cell seeding, i.e. re-attachment to the bladder wall of tumor cells which were dislocated during resection. Mitomycin was administered after TUR to 16 patients in the HAL group (5.9%) and to 20 patients in the white light group (7.1%).

Tumor recurrence rate in both patient groups were determined and the results are displayed in Table 2

TABLE 2

| | Tumor recurrence rate by group and BCG and/or mitomycin treatment | | |
|---|---|---|---|
| Group | Received no BCG and/or mitomycin | Received BCG and/or mitomycin | All |
| White light (n = 280) | 63.1% (130/206) | 36.5% (27/74) | 56.1% (157/280) |
| HAL (n = 271) | 49.0% (101/206) | 41.5% (27/65) | 47.2% (128/271) |

In the white light group the difference in recurrence rate between the patients who received and who did not receive BCG and/or mitomycin treatment was statistically significant with a p-value <0.001 (36.5% versus 63.1%) which demonstrates the efficacy of BCG and/or mitomycin in preventing bladder cancer recurrence.

In the HAL group, however, the efficacy of these treatments could not be demonstrated, since the difference in recurrence rate between the patients who received and who did not receive BCG and/or mitomycin was not statistically significant (p-value=0.291, 41.5% versus 49.0%). This absence of significant BCG and/or mitomycin treatment effect is mainly due to pronounced reduced tumor recurrence rate in patients wo did not receive BCG and/or mitomycin (49.0% versus 63.1%) and this reduction in tumor recurrence rate could possibly be explained by a therapeutic effect of HAL (HAL PDT effect) which results in the prevention of bladder cancer recurrence.

Various Embodiments of the Invention are as Follows:

Embodiment 1: Composition comprising hexyl 5-ALA ester (HAL) or a pharmaceutically acceptable salt thereof for use in a method of photodynamic therapy for bladder cancer, wherein said composition is instilled into the bladder of a patient in need of such treatment and the inside of said bladder is exposed to blue light having a fluence rate of 1.5 to 12.5 mW/cm$^2$.

Embodiment 2: Composition for use according to Embodiment 1, wherein the blue light is provided at a light dose of 0.2 to 15.0 J/cm$^2$.

Embodiment 3: Composition for use according to Embodiment 1 or 2, wherein the inside of the bladder is exposed to blue light having a fluence rate of 2.5 to 7.0 mW/cm$^2$.

Embodiment 4: Composition for use according to Embodiment 3, wherein the blue light is provided at a light dose of 0.3 to 8.0 J/cm$^2$.

Embodiment 5: Composition for use according to any of Embodiments 1 to 4, wherein the inside of said bladder is further exposed to white light having a fluence rate of 3.0 to 22.0 mW/cm$^2$.

Embodiment 6: Composition for use according to Embodiment 5, wherein said white light is provided at a light dose of 0.4 to 26.5 J/cm$^2$.

Embodiment 7: Composition for use according to Embodiment 5, wherein said inside of the bladder is exposed to white light having a fluence rate of 5.0 to 12.5 mW/cm$^2$.

Embodiment 8: Composition for use according to Embodiment 7, wherein said white light is provided at a light dose of 0.6 to 15.0 J/cm$^2$.

Embodiment 9: Composition for use according to any of Embodiments 1 to 8, wherein said composition is an aqueous solution of HAL, preferably a solution of HAL in an aqueous buffer, more preferably a solution of HAL in a phosphate buffer.

Embodiment 10: Composition for use according to Embodiment 9, wherein the pH of said composition is in the range of 4.5 to 7.5, preferably in the range of 5.7 to 7.2.

Embodiment 11: Composition for use according to any of Embodiments 1 to 10, wherein said composition is a solution of 2 mg/ml HAL hydrochloride in an aqueous buffer comprising disodium phosphate dehydrate, potassium dihydrogen phosphate, sodium chloride, hydrochloric acid, sodium hydroxide and water.

Embodiment 12: Composition for use according to any of Embodiments 5 to 11, wherein said inside of the bladder is first exposed to white light and then to blue light.

Embodiment 13: Composition for use according to any of Embodiments 1 to 12, wherein a blue-light cystoscope is used as a light source to provide and blue light or said blue and white light.

Embodiment 14: Composition for use according to Embodiment 13, wherein said blue-light cystoscope is a commercially available blue-light cystoscope.

Embodiment 15: Composition for use according to any of Embodiments 1 to 14, wherein the inside of the bladder is exposed to blue light or to blue and white light for a period of 2 to 20 minutes.

Embodiment 16: Composition for use according to any of Embodiments 1 to 15 for use in a method of treating bladder cancer wherein said method of photodynamic therapy is used as adjuvant therapy.

Embodiment 17: Composition for use according to Embodiment 16, wherein said bladder cancer is NMIBC and said method of photodynamic therapy is simultaneously carried out with a transurethral resection of NMIBC.

Embodiment 18: Composition for use according to Embodiment 16, wherein said bladder cancer is NMIBC and said method of photodynamic therapy is carried in a patient having undergone transurethral resection of NMIBC.

Embodiment 19: Composition for use according to Embodiments 16-18, wherein said method of photodynamic therapy replaces or partially replaces other adjuvant therapies.

Embodiment 20: Composition for use according to Embodiment 19, wherein said other adjuvant therapies are chemotherapy and/or immunotherapy, preferably BCG treatment.

Embodiment 21: Composition for use according to Embodiment 19, wherein said method of photodynamic therapy is carried out in BCG refractory patients.

Embodiment 22: Composition for use according to any of Embodiments 1 to 15 for use in a method of treating bladder cancer wherein said method of photodynamic therapy is used as neoadjuvant therapy.

Embodiment 23: Composition for use according to Embodiment 22, wherein said bladder cancer is MIBC.

Embodiment 24: Composition for use according to Embodiment 23, wherein said method of photodynamic therapy is carried out prior to a cystectomy.

Embodiment 25: Composition for use according to Embodiment 24, wherein the cystectomy is carried out directly after the method of photodynamic therapy.

Embodiment 26: Method of photodynamic therapy for bladder cancer comprising the instillation into the bladder of a patient in need of such treatment of a composition comprising hexyl 5-ALA ester (HAL) or a pharmaceutically acceptable salt thereof and exposing the inside of said bladder to blue light having a fluence rate of 1.5 to 12.5 mW/cm$^2$.

Embodiment 27: Method according to Embodiment 26, wherein the blue light is provided at a light dose of 0.2 to 15.0 J/cm$^2$.

Embodiment 28: Method according to Embodiment 26 or 27, wherein the inside of the bladder is exposed to blue light having a fluence rate of 2.5 to 7.0 mW/cm$^2$.

Embodiment 29: Method according to Embodiment 28, wherein the blue light is provided at a light dose of 0.3 to 8.0 J/cm$^2$.

Embodiment 30: Method according to any of Embodiments 26 to 29, wherein the inside of said bladder is further exposed to white light having a fluence rate of 3.0 to 22.0 mW/cm$^2$.

Embodiment 31: Method according to Embodiment 30, wherein said white light is provided at a light dose of 0.4 to 26.5 J/cm$^2$.

Embodiment 32: Method according to Embodiment 30, wherein said inside of the bladder is exposed to white light having a fluence rate of 5.0 to 12.5 mW/cm$^2$.

Embodiment 33: Composition for use according to Embodiment 32, wherein said white light is provided at a light dose of 0.6 to 15.0 J/cm$^2$.

Embodiment 34: Method according to any of Embodiments 26 to 33, wherein said composition is an aqueous solution of HAL, preferably a solution of HAL in an aqueous buffer, more preferably a solution of HAL in a phosphate buffer.

Embodiment 35: Method according to Embodiment 34, wherein the pH of said composition is in the range of 4.5 to 7.5, preferably in the range of 5.7 to 7.2.

Embodiment 36: Method according to any of Embodiments 26 to 35, wherein said composition is a solution of 2 mg/ml HAL hydrochloride in an aqueous buffer comprising disodium phosphate dehydrate, potassium dihydrogen phosphate, sodium chloride, hydrochloric acid, sodium hydroxide and water.

Embodiment 37: Method according to any of Embodiments 30 to 36, wherein said inside of the bladder is first exposed to white light and then to blue light.

Embodiment 38: Method according to any of Embodiments 26 to 37, wherein a blue-light cystoscope is used as a light source to provide and blue light or said blue and white light.

Embodiment 39: Method according to Embodiment 38, wherein said blue-light cystoscope is a commercially available blue-light cystoscope.

Embodiment 40: Method according to any of Embodiments 26 to 39, wherein the inside of the bladder is exposed to blue light or to blue and white light for a period of 2 to 20 minutes.

Embodiment 41: Method according to any of Embodiments 26 to 40 for use in a method of treating bladder cancer wherein said method of photodynamic therapy is used as adjuvant therapy.

Embodiment 42: Method according to Embodiment 41, wherein said bladder cancer is NMIBC and said method of photodynamic therapy is simultaneously carried out with a transurethral resection of NMIBC.

Embodiment 43: Method according to Embodiment 41, wherein said bladder cancer is NMIBC and said method of photodynamic therapy is carried in a patient having undergone transurethral resection of NMIBC.

Embodiment 44: Method according to Embodiments 41 to 43, wherein said method of photodynamic therapy replaces or partially replaces other adjuvant therapies.

Embodiment 45: Method according to Embodiment 44, wherein said other adjuvant therapies are chemotherapy and/or immunotherapy, preferably BCG treatment.

Embodiment 46: Method according to Embodiment 44, wherein said method of photodynamic therapy is carried out in BCG refractory patients.

Embodiment 47: Method according to any of Embodiments 26 to 40 for use in a method of treating bladder cancer wherein said method of photodynamic therapy is used as neoadjuvant therapy.

Embodiment 48: Method according to Embodiment 47, wherein said bladder cancer is MIBC.

Embodiment 49: Method according to Embodiment 48, wherein said method of photodynamic therapy is carried out prior to a cystectomy.

Embodiment 50: Method according to Embodiment 49, wherein the cystectomy is carried out directly after the method of photodynamic therapy.

The invention claimed is:

1. A method of photodynamic therapy used as adjuvant therapy in the treatment of non-muscle invasive bladder cancer (NMIBC), wherein said method of photodynamic therapy is carried out in a patient undergoing or having undergone transurethral resection of NMIBC, said method comprising the instillation into the bladder of said patient of a composition in the form of an aqueous solution comprising hexyl 5-ALA ester (HAL) or a pharmaceutically acceptable salt thereof in a concentration of 0.1 to 5% by weight of the total weight of the composition and exposing the inside of said bladder to blue light having a fluence rate of 1.5 to 12.5 mW/cm$^2$ and wherein the blue light is provided at a light dose of 0.2 to 15.0 J/cm$^2$.

2. The method according to claim 1, wherein the inside of the bladder is exposed to blue light having a fluence rate of 2.5 to 7.0 mW/cm$^2$.

3. The method according to claim 2, wherein the blue light is provided at a light dose of 0.3 to 8.0 J/cm$^2$.

4. The method according to claim 1, wherein the blue light is provided at a light dose of 0.3 to 8.0 J/cm$^2$.

5. The method according to claim 1, wherein the inside of said bladder is further exposed to white light having a fluence rate of 3.0 to 22.0 mW/cm$^2$.

6. The method according to claim 5, wherein said white light is provided at a light dose of 0.4 to 26.5 J/cm$^2$.

7. The method according to claim 5, wherein said inside of the bladder is exposed to white light having a fluence rate of 5.0 to 12.5 mW/cm$^2$.

8. The method according to claim 7, wherein said white light is provided at a light dose of 0.6 to 15.0 J/cm$^2$.

9. The method according to claim 5, wherein said inside of the bladder is first exposed to white light and then to blue light.

10. The method according to claim 5, wherein a blue-light cystoscope is used as a light source to provide said blue light and said white light.

11. The method according to claim 5, wherein the inside of the bladder is exposed to blue light and white light for a period of 2 to 20 minutes.

12. The method according to claim 5, wherein said method of photodynamic therapy replaces or partially replaces other adjuvant therapies.

13. The method according to claim 12, wherein said other adjuvant therapies are chemotherapy and/or immunotherapy.

14. The method according to claim 12, wherein said other adjuvant therapy is BCG treatment.

15. The method according to claim 5, wherein said method of photodynamic therapy is carried out in BCG refractory patients.

16. The method according to claim 1, wherein said composition is a solution of HAL in an aqueous buffer.

17. The method according to claim 16, wherein the aqueous buffer is a phosphate buffer.

18. The method according to claim 16, wherein the pH of said composition is in the range of 4.5 to 7.5.

19. The method according to claim 16, wherein said composition is a solution of 2 mg/ml HAL hydrochloride in an aqueous buffer comprising disodium phosphate dehydrate, potassium dihydrogen phosphate, sodium chloride, hydrochloric acid, sodium hydroxide and water.

20. The method according to claim 1, wherein a blue-light cystoscope is used as a light source to provide said blue light.

21. The method according to claim 20, wherein said blue-light cystoscope is a commercially available blue-light cystoscope.

22. The method according to claim 1, wherein the inside of the bladder is exposed to blue light for a period of 2 to 20 minutes.

23. The method according to claim 1, wherein said method of photodynamic therapy replaces or partially replaces other adjuvant therapies.

24. The method according to claim 23, wherein said other adjuvant therapies are chemotherapy and/or immunotherapy.

25. The method according to claim 23, wherein said other adjuvant therapy is Bacillus Calmette-Guerin (BCG) treatment.

26. The method according to claim 1, wherein said method of photodynamic therapy is carried out in BCG refractory patients.

* * * * *